United States Patent
Hibst et al.

(10) Patent No.: US 6,737,545 B1
(45) Date of Patent: May 18, 2004

(54) MULTI-METAL OXIDE COMPOUNDS WITH A TWO-PHASE STRUCTURE

(75) Inventors: Hartmut Hibst, Schriesheim (DE); Signe Unverricht, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/646,884

(22) PCT Filed: Mar. 26, 1999

(86) PCT No.: PCT/EP99/02083

§ 371 (c)(1),
(2), (4) Date: Oct. 6, 2000

(87) PCT Pub. No.: WO99/51342

PCT Pub. Date: Oct. 14, 1999

(30) Foreign Application Priority Data

Apr. 6, 1998 (DE) .......................................... 198 15 280

(51) Int. Cl.⁷ .......................... C07C 51/235; B01J 23/20
(52) U.S. Cl. ........................................ 562/535; 502/353
(58) Field of Search ................................. 562/535, 353

(56) References Cited

U.S. PATENT DOCUMENTS

| | | |
|---|---|---|
| 4,075,127 A | 2/1978 | Kadowaki et al. |
| 4,469,357 A | 9/1984 | Martin |
| 5,446,004 A | 8/1995 | Tenten et al. |
| 5,493,052 A | 2/1996 | Tenten et al. |
| 5,521,137 A * | 5/1996 | Martin et al. |
| 5,686,373 A | 11/1997 | Tenten et al. |
| 5,739,392 A | 4/1998 | Tanimoto et al. |
| 5,885,922 A | 3/1999 | Hibst et al. |

FOREIGN PATENT DOCUMENTS

| | | |
|---|---|---|
| DE | 26 35 031 | 7/1977 |
| DE | 43 02 991 | 8/1994 |
| DE | 0686600 A1 * | 12/1995 |
| DE | 195 28 646 | 2/1997 |
| DE | 197 40 493 | 3/1999 |
| EP | 0 811 597 | 12/1997 |

* cited by examiner

*Primary Examiner*—Johann Richter
*Assistant Examiner*—Paul A. Zucker
(74) *Attorney, Agent, or Firm*—Oblon, Spivak, McClelland, Maier & Neustadt, P.C.

(57) ABSTRACT

Multimetal oxide materials containing molybdenum, vanadium, antimony, one or more of the elements W, Nb, Ta, Cr and Ce and one or more of the elements Cu, Zn, Co, Fe, Cd, Mn, Mg, Ca, Sr and Ba and having a 2-component structure are used for the gas-phase catalytic oxidative preparation of acrylic acid.

14 Claims, No Drawings

MULTI-METAL OXIDE COMPOUNDS WITH A TWO-PHASE STRUCTURE

CONTINUING APPLICATION DATA

This application is a 371 of PCT/EP99/02083 filed on Mar. 26, 1999.

SUMMARY OF THE INVENTION

The present invention relates to multimetal oxide materials of the formula I $$(A)_p(B)_q \quad (I),$$

where:

A is $Mo_{12}V_aX^1_bX^2_cX^3_dX^4_eX^5_fX^6_gO_x$,

B is $X^7_1Sb_hH_iO_y$, $X^1$ is W, Nb, Ta, Cr and/or Ce, preferably W, Nb and/or Cr, $X^2$ is Cu, Ni, Co, Fe, Mn and/or Zn, preferably Cu, Ni, Co and/or Fe, $X^3$ is Sb and/or Bi, preferably Sb, $X^4$ is Li, Na, K, Rb, Cs and/or H, preferably Na and/or K, $X^5$ is Mg, Ca, Sr and/or Ba, preferably Ca, Sr and/or Ba, $X^6$ is Si, Al, Ti and/or Zr, preferably Si, Al and/or Ti, $X^7$ is Cu, Zn, Co, Fe, Cd, Mn, Mg, Ca, Sr and/or Ba, preferably Cu, Ni, Zn, Co and/or Fe, particularly preferably Cu and/or Zn, very particularly preferably Cu, a is from 1 to 8, preferably from 2 to 6, b is from 0.2 to 5, preferably from 0.5 to 2.5, c is from 0 to 23, preferably from 0 to 4, d is from 0 to 50, preferably from 0 to 3, e is from 0 to 2, preferably from 0 to 0.3, f is from 0 to 5, preferably from 0 to 2, g is from 0 to 50, preferably from 0 to 20, h is from 0.1 to 50, preferably from 0.2 to 20, particularly preferably from 0.2 to 5, i is from 0 to 50, preferably from 0 to 20, particularly preferably from 0 to 12, x and y are each numbers which are determined by the valency and frequency of the elements in (I) other than oxygen and p and q are each numbers which differ from zero and the ratio p/q is from 20:1 to 1:80, preferably from 10:1 to 1:35, particularly preferably from 2:1 to 1:3, which contain the moiety $(A)_p$ in the form of three-dimensional regions A of the chemical composition A: $Mo_{12}V_aX^1_bX^2_cX^3_dX^4_eX^5_fX^6_gO_x$ and the moiety $(B)_q$ in the form of three-dimensional regions B of the chemical composition B: $X^7_1Sb_hH_iO_y$ where the regions A, B are distributed relative to one another as in a mixture of finely divided A and finely divided B, with the proviso that the multimetal oxide materials (I) are prepared using at least one separately preformed oxometallate B, $X^7_1Sb_hH_iO_y$, which is obtainable by preparing a dry blend from suitable sources of the elemental constituents of the oxometallate B which contain at least a part of the antimony in the oxidation state +5 and calcining said dry blend at from 200 to 1200° C., preferably from 200 to 850° C., particularly preferably from 250 to <600° C., frequently ≦550° C.

The present invention also relates to processes for the preparation of multimetal oxide materials (I) and their use as catalysts for the gas-phase catalytic oxidation of acrolein to acrylic acid.

DESCRIPTION OF THE BACKGROUND

WO 96/27437 relates to multimetal oxide materials which contain the elements Mo, V, Cu and Sb as essential components and whose X-ray diffraction pattern has the line of strongest intensity at a 2θ value of 22.2°. WO 96/27437 recommends these multimetal oxide materials as suitable catalysts for the gas-phase catalytic oxidation of acrolein to acrylic acid. Furthermore, WO 96/27437 recommends using $Sb_2O_3$ as an antimony source for the preparation of these multimetal oxide materials. Preparation of an antimony-containing component beforehand is not described in WO 96/27437.

EP-B 235760 relates to a process for the preparation of Sb, Mo, V and/or Nb-containing multimetal oxide materials which are suitable as catalysts for the gas-phase catalytic oxidation of acrolein to acrylic acid. EP-B 235760 recommends using an antimony prepared beforehand as an antimony source for the preparation of these multimetal oxide materials.

The disadvantage of the multimetal oxide materials of the prior art is that their activity and the selectivity of the acrylic acid formation are not completely satisfactory when they are used as catalysts for the gas-phase catalytic oxidation of acrolein to acrylic acid.

OBJECTS OF THE INVENTION

It is an object of the present invention to provide novel multimetal oxide materials which, when used as catalysts for the gas-phase catalytic oxidation of acrolein to acrylic acid, have the disadvantages of the catalysts of the prior art to a reduced extent, if at all.

We have found that this object is achieved by the multimetal oxide materials (I) defined at the outset.

Very particularly preferred materials (I) are those whose regions A have a composition of the following formula (II)

$$Mo_{12}V_{a'}X^1_{b'}X^2_{c'}X^5_{f'}X^6_{g'}O_{x'}, \quad (II),$$

where $X^1$ is W and/or Nb, $X^2$ is Cu and/or Ni, $X^5$ is Ca and/or Sr, $X^6$ is Si and/or Al, a' is 2 to 6, b' is 0.5 to 2.5, c' is 0 to 4, f' is 0 to 2, g' is 0 to 2 and x' is a number which is determined by the valency and frequency of the elements in (II) other than oxygen.

DETAILED DESCRIPTION OF THE INVENTION

It is also advantageous if at least one of the moieties $(A)_p$, $(B)_q$ of the novel multimetal oxide materials (I) is contained in the latter in the form of three-dimensional regions having the chemical composition A or B, whose maximum diameters $d_A$ and $d_B$ (longest connecting line between two points present on the surface (interface) of the region and passing through the center of gravity of the region), respectively, are from >0 to 300 μm, preferably from 0.01 to 100 μm, particularly preferably from 0.05 to 50 μm, very particularly preferably from 0.05 to 20 μm.

However, the maximum diameters can of course also be from 0.05 to 1.0 μm or from 75 to 125 μm (the experimental determination of the maximum diameter is permitted, for example, by a microstructure analysis by means of a scanning electron microscope (SEM)).

As a rule, the moiety $(B)_q$ is present in the novel multimetal oxide materials essentially in crystalline form, i.e. as a rule the regions B essentially comprise small crystallites whose maximum dimension is typically from 0.05 to 20 μm. However, the moiety $(B)_q$ can of course also be amorphous and/or crystalline.

Particularly preferred novel multimetal oxide materials are those whose regions B essentially comprise crystallites which have the trirutile structure type of α- and/or β-copper antimony $CuSb_2O_6$. α-$CuSb_2O_6$ crystallizes in a tetragonal trirutile structure (E.-O. Giere et al., J. Solid State Chem. 131 (1997), 263–274), whereas β-$CuSb_2O_6$ has a monoclinically distorted trirutile structure (A. Nakua et al., J. Solid State Chem. 91 (1991), 105–112, or reference diffraction pattern in index card 17-284 in the JCPDS-ICDD index 1989). In addition, regions B which have the pyrochlore structure of the mineral partzite, a copper antimony oxide hydroxide with the variable composition $Cu_ySb_{2-x}(O, OH, H_2O)_{6-7}(y \leq 2.0 \leq x \leq 1)$, are preferred (B. Mason et al., Mineral. Mag. 30 (1953), 100–112, or reference pattern in index card 7-303 of the JCPDS-ICDD index 1996).

Furthermore, the regions B may consist of crystallites which have the structure of copper antimony $Cu_9Sb_4O_{19}$ (S. Shimada et al., Chem. Lett. (1983) 1875–1876 or S. Shimada et al., Thermochim. Acta 133 (1988), 73–77 or reference pattern in index card 45-54 of the JCPDS-ICDD index) and/or the structure of $Cu_4SbO_{4.5}$ (S. Shimada et al., Thermochim. Acta 56 (1982), 73–82 or S. Shimada et al., Thermochim. Acta 133 (1988), 73–77, or reference pattern in index card 36-1106 of the JCPDS-ICDD index).

Of course, the regions B may also consist of crystallites which constitute a mixture of the abovementioned structures.

The novel materials (I) are obtainable in a simple manner, for example by first separately preforming oxometallates B,

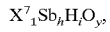
$X^7{}_1Sb_hH_iO_y$, in finely divided form as starting material 1. The oxometallates B can be prepared by preparing a preferably intimate, advantageously finely divided dry blend from suitable sources or their elemental constituents and calcining said dry blend at from 200 to 1200° C., preferably from 200 to 850° C., particularly preferably from 250 to <600° C., frequently ≦550° C. (as a rule for from 10 min to several hours). All that is essential to the invention is that at least a part of the oxometallates B of the starting material 1 (referred to below as oxometallates B*) is obtainable by preparing a preferably intimate, advantageously finely divided dry blend from suitable sources of the elemental constituents of the oxometallate B which contain at least a part of the antimony in oxidation state +5 and calcining said dry blend at from 200 to 1200° C., preferably from 200 to 850° C., particularly preferably from 250 to <600° C., frequently ≦550° C. (as a rule for from 10 min to several hours). The calcination of the precursors of the oxo-metallates B can generally also be carried out under inert gas, but also under a mixture of inert gas and oxygen, such as air, or under pure oxygen. Calcination under a reducing atmosphere is also possible. As a rule, the required calcination time decreases with increasing calcination temperature. Advantageously, the proportion of the oxometallates B* in the finely divided starting material 1 is at least 10, better at least 20, frequently at least 30 or at least 40, preferably at least 50, even better at least 60, particularly preferably at least 70 or at least 80, frequently at least 90 or 95, very particularly preferably 100, % by weight, based on the starting material 1.

Oxometallates B* are obtainable, for example, by the preparation methods described in detail in DE-A 24 076 77. Preferred among these is the procedure in which antimony trioxide and/or $Sb_2O_4$ are oxidized in an aqueous medium by means of hydrogen peroxide in an amount which is equal to or greater than the stoichiometric amount at from 40 to 100° C. to give antimony(V) oxide hydroxide, aqueous solutions and/or suspensions of suitable starting compounds of the other elemental constituents of the oxometallate B* are added just before this oxidation, during this oxidation and/or after this oxidation, the resulting aqueous mixture is then dried (preferably spray-dried (inlet temperature: from 250 to 600° C., outlet temperature: from 80 to 130° C.)) and the intimate dry blend is then calcined as described.

In the process just described, for example, aqueous hydrogen peroxide solutions having an $H_2O_2$ content from 5 to 33 or more % by weight may be used. Subsequent addition of suitable starting compounds of the other elemental constituents of the oxometallate B* is recommended in particular when these are capable of catalytically decomposing the hydrogen peroxide. However, it would of course also be possible to isolate the resulting antimony(V) oxide hydroxide from the aqueous medium and to intimately dry-blend it, for example, with suitable finely divided starting compounds of the other elemental constituents of the oxometallate B* and then to calcine this intimate mixture as described.

It is important that the elemental sources of the oxometallates B, B* are either already oxides or are compounds which can be converted into oxides by heating, in the presence or absence of oxygen.

In addition to the oxides, particularly suitable starting compounds are therefore halides, nitrates, formates, oxalates, acetates, carbonates and/or hydroxides (compounds such as $NH_4OH$, $NH_4CHO_2$, $CH_3COOH$, $NH_4CH_3CO_2$ or ammonium oxalate, which disintegrate and/or can be decomposed at the latest during calcination to give compounds which escape completely in gaseous form, may additionally be incorporated). For the preparation of oxometallates B, the intimate mixing of the starting compounds can generally be carried out in dry or in wet form. If it is effected in dry form, the starting compounds are advantageously used in the form of finely divided powders. However, the intimate mixing is preferably effected in wet form. Usually, the starting compounds are mixed with one another in the form of an aqueous solution and/or suspension. After the end of the mixing process, the fluid material is dried and is calcined after drying. The drying is preferably carried out by spray-drying.

After calcination is complete, the oxometallates B, B* can be comminuted again (for example by wet or dry milling, for example in a ball mill or by jet-milling) and the particle class, having a maximum particle diameter (as a rule from >0 to 300 μm, usually from 0.01 to 200 μm, preferably from 0.01 to 100 μm, very particularly preferably from 0.05 to 20 μm) in the maximum diameter range desired for the novel multimetal oxide (I) can be separated off from the resulting powder, frequently essentially comprising spherical particles, by classification to be carried out in a manner known per se (for example wet or dry sieving).

A preferred method of preparation of oxometallates B* of the formula $(Cu,Zn)_1Sb_hH_iO_y$ comprises converting antimony trioxide and/or $Sb_2O_4$ in an aqueous medium by means of hydrogen peroxide initially into a preferably finely divided Sb(V) compound, for example Sb(V) oxide hydroxide hydrate, adding an ammoniacal aqueous solution of zinc carbonate and/or copper carbonate (which may have, for example, the composition $Cu_2(OH)_2CO_3$) to the resulting aqueous suspension, drying the resulting aqueous mixture, for example spray-drying it in the manner described, and calcining the resulting powder in the manner described, if necessary after subsequent kneading with water followed by extrusion and drying.

In the case of oxometallates B differing from oxometallates B*, it proves particularly advantageous to start from an aqueous antimony trioxide suspension and to dissolve therein the $X^7$ elements as nitrate and/or acetate, to spray-dry the resulting aqueous mixture in the manner described and then to calcine the resulting powder in the manner described.

For the preparation of multimetal oxide materials (I), the starting materials 1 preformed as described can then be brought into intimate contact with suitable sources of the elemental constituents of the multimetal oxide material A

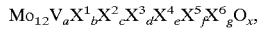

$Mo_{12}V_aX^1_bX^2_cX^3_dX^4_eX^5_fX^6_gO_x,$ in the desired ratio and a dry blend resulting therefrom can be calcined at from 250 to 500° C., it being possible to carry out the calcination under inert gas (e.g. $N_2$), a mixture of inert gas and oxygen (e.g. air), reducing gases such as hydrocarbons (e.g. methane), aldehydes (e.g. acrolein) or ammonia, or under a mixture of $O_2$ and reducing gases (e.g. all of the abovementioned ones), as described, for example, in DE-A 43 359 73. In the case of calcination under reducing conditions, it should be ensured that the metallic constituents are not reduced right down to the element. The calcination time is as a rule a few hours and usually decreases with increasing calcination temperature. As is generally known, all that is important with regard to the sources of the elemental constituents of the multimetal oxide material A is that either they are already oxides or they are compounds which can be converted into oxides by heating, at least in the presence of oxygen. In addition to the oxides, particularly suitable starting compounds are halides, nitrates, formates, oxalates, citrates, acetates, carbonates or hydroxides. Suitable starting compounds of Mo, V, W and Nb are also their oxo compounds (molybdates, vanadates, tungstates and niobates) or the acids derived from these.

The starting material 1 can be brought into intimate contact with the sources of the multimetal oxide material A (starting material 2) either in dry or in wet form. In the latter case, it is merely necessary to ensure that the preformed multimetal oxides B, B* do not go into solution. In an aqueous medium, the latter is usually ensured at a pH which does not differ too greatly from 7 and at $\leq 60°$ C. and $\leq 40°$ C., respectively. If said substances are brought into intimate contact in wet form, drying is then usually carried out to give a dry material (preferably by spray-drying). Such a dry material is automatically obtained in dry blending.

Possible mixing methods are thus, for example:

a. mixing a dry, finely divided, preformed starting material 1 with dry, finely divided starting compounds of the elemental constituents of the desired multimetal oxide A in the desired ratio in a mixer, kneader or mill;

b. preforming a finely divided multimetal oxide A by intimate mixing of suitable starting compounds of its elemental constituents (dry or wet) and then calcining the resulting intimate dry blend at from 250 to 500° C. (regarding the calcination time, calcination atmosphere and element sources, statements made above are applicable); converting the preformed multimetal oxide A into finely divided form and mixing it with the finely divided starting material 1 in the desired ratio as in a.; in this mixing method, a final calcination of the resulting mixture is not essential;

c. stirring the required amount of preformed starting material 1 into an aqueous solution and/or suspension of starting compounds of the elemental constituents of the desired multimetal oxide A and then spray-drying the mixture; instead of the starting compounds of the elemental constituents of the desired multimetal oxide A, it is of course also possible to use a multimetal oxide A itself, already preformed according to b.

All mixing methods between a., b. and/or c. can of course also be used. The resulting intimate dry blend can then be calcined in the manner described and then shaped to give the desired catalyst geometry, or vice versa. In principle, the calcined dry blend (or possibly uncalcined dry blend where mixing method b. is used) can however also be used in the form of a powder catalyst.

Our own investigations have shown that, on calcination of the dry blend comprising the starting material 1 and the starting material 2, essentially no fusion of the components of the starting material 1 with those of the starting material 2 takes place and the structure type of the crystallites contained in the starting material 1 are often essentially retained as such.

As indicated above, this opens up the possibility, after milling of the preformed starting mixture 1, to separate off the particle class having the maximum particle diameter (as a rule from >0 to 300 $\mu$m, preferably from 0.01 to 100 $\mu$m, particularly preferably from 0.05 to 20 $\mu$m) in the maximum diameter range desired for the multimetal oxide material (I) from the resulting powder, frequently comprising essentially spherical particles, by a classification to be carried out in a manner known per se (for example wet or dry sieving) and thus to use said particle class in a tailor-made manner for the preparation of the desired multimetal oxide material.

When the novel multimetal oxide materials (I) are used as catalysts for the gas-phase catalytic oxidation of acrolein to acrylic acid, the shaping to give the desired catalyst geometry is preferably carried out by application to preformed inert catalyst carriers, it being possible to effect the application before or after the final calcination. The conventional carrier materials, such as porous or nonporous aluminas, silica, thorium dioxide, zirconium dioxide, silicon carbide or silicates such as magnesium silicate or aluminum silicate, may be used. The supports may be regularly or irregularly shaped, regularly shaped supports having pronounced surface roughness, for example spheres or hollow cylinders, being preferred. Among these, in turn, spheres are particularly advantageous. It is particularly advantageous to use essentially nonporous spherical steatite carriers with a rough surface, whose diameter is from 1 to 8 mm, preferably from 4 to 5 mm. The layer thickness of the active material is advantageously chosen in the range from 50 to 500 $\mu$m, preferably from 150 to 250 $\mu$m. It should be pointed out here that, for coating the supports, in the preparation of such coated catalysts, the powder material to be applied is as a rule moistened and, after application, is dried, for example by means of hot air.

For the preparation of the coated catalysts, the coating of the supports is as a rule carried out in a suitable rotatable container, as previously disclosed, for example, in DE-A 2909671 or in EP-A 293859. As a rule, the relevant material is calcined before coating the carrier.

The coating and calcination process according to EP-A 293 859 can be used in a suitable manner known per se so that the resulting multimetal oxide active materials have a specific surface area of from 0.50 to 150 $m^2/g$, a specific pore volume of from 0.10 to 0.90 $cm^3/g$ and a pore diameter distribution such that at least 10% of the total pore volume is associated with each of the diameter ranges from 0.1 to <1 $\mu m$, from 1.0 to <10 $\mu m$ and from 10 $\mu m$ to 100 $\mu m$. Moreover, the pore diameter distributions stated as being preferred in EP-A 293 859 may be established.

The novel multimetal oxide materials can of course also be operated as unsupported catalysts. In this respect, the intimate dry blend comprising the starting materials 1 and 2 is preferably compacted directly to give the desired catalyst geometry (for example by means of pelleting or extrusion), it being possible, if necessary, to add conventional assistants, for example graphite or stearic acid as lubricants, and/or molding assistants and reinforcing agents, such as microfibers of glass, asbestos, silicon carbide or potassium titanate, and calcined. Here, too, calcination can in general be effected prior to shaping. Preferred geometries for unsupported catalysts are hollow cylinders having an external diameter and a length of from 2 to 10 mm and a wall thickness of from 1 to 3 mm.

The novel multimetal oxide materials are particularly suitable as catalysts having high activity and selectivity (at given conversion) for the gas-phase catalytic oxidation of acrolein to acrylic acid. Acrolein produced by the catalytic gas-phase oxidation of propene is usually used in the process. As a rule, the acrolein-containing reaction gases from this propene oxidation are used without intermediate purification. Usually, the gas-phase catalytic oxidation of acrolein is carried out in tube-bundle reactors as a heterogeneous fixed-bed oxidation. Oxygen, advantageously diluted with inert gases (for example in the form of air), is used as an oxidizing agent in a manner known per se. Suitable diluent gases are, for example, $N_2$, $CO_2$, hydrocarbon, recycled reaction exit gases and/or steam. As a rule, an acrolein:oxygen:steam:inert gas volume ratio of 1:(1 to 3):(0 to 20):(3 to 30), preferably 1:(1 to 3):(0,5 to 10):(7 to 18), is established in the acrolein oxidation. The reaction pressure is in general from 1 to 3 bar and the total space velocity is preferably from 1000 to 3500 l(S.T.P.)/l/h. Typical multitube fixed-bed reactors are described, for example, in DE-A 2830765, DE-A 2 201 528 or U.S. Pat. No. 3,147,084. The reaction temperature is usually chosen so that the acrolein conversion in a single pass is above 90%, preferably above 98%. Usually, reaction temperatures of from 230 to 330° C. are required in this respect.

In addition to the gas-phase catalytic oxidation of acrolein to acrylic acid, the novel products are however also capable of catalyzing the gas-phase catalytic oxidation of other organic compounds, in particular other alkanes, alkanols, alkanals, alkenes and alkenols, preferably with 3 to 6 carbon atoms (e.g. propylene, methacrolein, tert-butanol, the methyl ether of tert-butanol, isobutene, isobutane or isobutyraldehyde), to olefinically unsaturated aldehydes and/or carboxylic acids, and the corresponding nitriles (ammoxidation, especially of propene to acrylonitrile and of isobutene or tert-butanol to methacrylonitrile). The preparation of acrolein, methacrolein and methacrylic acid may be mentioned by way of example. However, they are also suitable for the oxidative dehydrogenation of olefinic compounds.

Unless stated otherwise, the conversion, selectivity and residence time are defined in this publication as follows:

$$\text{Conversion } C \text{ of acrolein (\%)} = \frac{\text{no. of moles of acrolein converted}}{\text{no. of moles of acrolein used}} \times 100;$$

$$\text{Selectivity } S \text{ of the acrylic acid formation \%} = \frac{\text{no. of moles of acrolein converted into acrylic acid}}{\text{total no. of moles of acrolein converted}} \times 100;$$

$$\text{Residence time (sec)} = \frac{\text{empty reactor volume filled with catalyst } (l)}{\text{Synthesis gas throughput } l(S.T.P.)/h} \times 3600.$$

EXAMPLES

I. Catalyst Preparation

Example a) Preparation of the Starting Material 1

946.0 g of $Sb_2O_3$ having an Sb content of 83.0% by weight were suspended in 4 l of water while stirring. 822.4 g of a 30% strength by weight aqueous $H_2O_2$ solution were added at room temperature (25° C.). Thereafter, the suspension was heated to 100° C. in the course of 1 hour with further stirring and was refluxed at this temperature for 5 hours. A solution of 595.6 g of $Cu(CH_3COO)_2.H_2O$ having a Cu content of 32.0% by weight in 4 l of water was then added to the aqueous suspension at 100° C. in the course of 30 minutes, the temperature of the total aqueous mixture decreasing to 60° C. At this temperature, 407.9 g of a 25% strength by weight aqueous ammonia solution were then added. Thereafter, the aqueous suspension was stirred for a further 2 hours at 80° C. and then cooled to room temperature (25° C.). Finally, the aqueous suspension was spray-dried (inlet temperature: 350° C., outlet temperature: 110° C.). The resulting spray-dried powder was heated stepwise in a rotary oven (2 l internal volume) with the passage of 100 l(S.T.P.)/h of air, initially to 150° C. in the course of 1 hour, then to 200° C. in the course of 4 hours and finally to 300° C. in the course of 2 hours, and was kept at the last-mentioned temperature for 1 hour. Thereafter, the powder obtained was heated to 400° C. in the course of 1.5 hours and thermostatted at this temperature for 1 hour. The powder obtained had a specific BET surface area (determined according to DIN 66131, by gas adsorption ($N_2$) according to Brunauer-Emmet-Teller) of 48.5 $m^2/g$ and the stoichiometry $CuSb_{2.15}O_y$ ($y \leq 6.375$). The powder exhibited the X-ray diffraction reflections of the mineral partzite and thus corresponded to reference spectrum 7-0303 of the JCPDS-ICDD index 1996.

b) Preparation of the Starting Material 2

682.4 g of ammonium heptamolybdate tetrahydrate (81.5% by weight of $MoO_3$), 131.0 g of ammonium metavanadate (77.3% by weight of $V_2O_5$) and 114.6 g of ammonium paratungstate heptahydrate (89.0% by weight of $WO_3$) were dissolved in succession in 5030 g of water at 95° C. The aqueous solution (starting material 2) was thus based on the following stoichiometry:

$Mo_{3.86}V_{1.11}W_{0.44} \hat{=} (MO_{12}V_{3.45}W_{1.37})_{0.32}.$ c) Preparation of a Multimetal Oxide Material M and of a Coated Catalyst CC The clear, orange-colored solution obtained above (starting material 2) was cooled to 25° C. and 150.0 g of ammonium acetate were added. 239.5 g of the starting material 1 were stirred into the aqueous solution cooled to 25° C. so that the molar ratio of the abovementioned stoichiometric units was 0.56 (starting material 1) to 0.32 (starting material 2). The resulting suspension was stirred for a further 1 hour at 25° C. and the aqueous mixture was then spray-dried. The spray-dried powder was then kneaded with a mixture of 70% by weight of water and 30% by weight of acetic acid (0.35 kg of liquid/kg of spray-dried powder) (LUK 2.5 kneader from Werner und Pfleiderer). The kneaded material obtained was dried for 16 hours at 110° C. in a through-circulation oven through which air flowed. The subsequently comminuted kneaded material was calcined in a cylindrical rotary oven (internal diameter: 12.5 cm, heated length: 50 cm) through which an air/nitrogen mixture (15 l(S.T.P.)/h of air and 200 l(S.T.P.)/h of nitrogen) flowed. 700 g of material to be calcined were introduced into the heated zone of the rotary oven. In the calcination, heating was initially carried out to 325° C. in the course of 60 minutes and this temperature was then maintained for 4 hours. Thereafter, heating was carried out to 400° C. in the course of 20 minutes and this temperature was maintained for 1 hour. The resulting catalytically active multimetal oxide material had the following gross stoichiometry:

$$Mo_{3.86}V_{1.11}W_{0.44}Cu_{0.56}Sb_{1.20}O_x \equiv (Mo_{12}V_{3.45}W_{1.37})_{0.32}(CuSb_{2.15}O_y)_{0.56}.$$

After the calcined active material had been milled, it was used to coat nonporous steatite spheres having a rough surface and a diameter of from 4 to 5 mm in a rotating drum, in an amount of 60 g of active powder per 400 g of steatite spheres, with simultaneous addition of water (coating process according to DE-A 4 442 346). The coated catalyst CC obtained was then dried with air at 110° C.

Comparative Example

The preparation of a comparative multimetal oxide material CM and of a comparative coated catalyst CCC was carried out as in the example, except that no hydrogen peroxide was used for the preparation of the starting material 1.

II. Use of the Coated Catalysts from I. as Catalysts for the Gas-phase Oxidation of Acrolein to Acrylic Acid The coated catalysts were introduced into a tubular reactor (V2A stainless steel, 25 mm internal diameter, 2000 g catalyst bed, heated by means of a salt bath) and, with the use of a residence time of 2.0 seconds, were loaded with a gaseous mixture having the composition 5% by volume of acrolein, 7% by volume of oxygen, 10% by volume of steam and 78% by volume of nitrogen.

The salt bath temperature was always adjusted so that, after forming was complete, a standard acrolein conversion C of 99% resulted after a single pass. The product gas mixture flowing from the reactor was analyzed by gas chromatography. The results of the selectivity of the acrylic acid formation using the various catalysts and the required salt bath temperatures are shown in the table below:

| Catalyst | Salt bath temperature (° C.) | S% |
| --- | --- | --- |
| CC | 267 | 95.5 |
| CCC | 272 | 93.8 |

We claim:
1. A multimetal oxide material of the formula I

$$(A)_p(B)_q \qquad (I),$$

where:

A is $Mo_{12}V_aX^1_bX^2_cX^3_dX^4_eX^5_fX^6_gO_x$

B is $X^7_iSb_hH_iO_y$, $X^1$ is W, Nb, Ta, Cr and/or Ce, $x^2$ is Cu, Ni, Co, Fe, Mn and/or Zn, $x^3$ is Sb and/or Bi, $x^4$ is Li, Na, K, Rb, Cs and/or H, $x^5$ is Mg, Ca, Sr and/or Ba, $x^6$ is Si, Al, Ti and/or Zr, $X^7$ is Cu, Zn, Co, Fe, Cd, Mn, Mg, Ca, Sr and/or Ba, a is from 1 to 8, b is from 0.2 to 5, c is from 0 to 23, d is from 0 to 50, e is from 0 to 2, f is from 0 to 5, g is from 0 to 50, h is from 0.1 to 50, i is from 0 to 50, x and y are each numbers which are determined by the valency and frequency of the elements in (I) other than oxygen and p and q are each numbers which differ from zero and the ratio p/q is from 20:1 to 1:80, which contains the moiety $(A)_p$ in the form of three-dimensional regions A of the chemical composition A: $Mo_{12}V_aX^1_bX^2_cX^3_dX^4_eX^5_fX^6_gO_x$ and the moiety $(B)_q$ in the form of three-dimensional regions B of the chemical composition B: $X^7_iSb_hH_iO_y$ where the regions A, B are distributed relative to one another as in a mixture of finely divided A and finely divided B, with the proviso that the multimetal oxide materials (I) are prepared using at least one separately preformed oxometallate B, $X^7_iSb_hH_iO_y$, which is obtained by preparing a dry blend from suitable sources of the elemental constituents of the oxometallate B which contain at least a part of the antimony in the oxidation state +5 and calcining said dry blend at from 200 to 1200° C.

2. A process for the preparation of a multimetal oxide as claimed in claim 1, in which an oxometallate B $X^7_iSb_hH_iO_y$, is preformed in finely divided form and then processed with sources of the elemental constituents of the multimetal oxide material A $Mo_{12}V_aX^1_bX^2_cX^3_dX^4_eX^5_fX^6_gO_x$, in the desired ratio to give a dry blend and the latter is calcined at from 250 to 500° C., wherein at least a portion of the oxometallate B is obtained by preparing a dry blend from sources of the elemental constituents of the oxometallate B which contain at least a part of the antimony in oxidation state +5 and calcining said dry blend at from 200 to 1200° C.

3. A process for the preparation of an oxometallate B of the formula $$X^7{}_t Sb_h H_i O_y,$$

where:

$X^7$ is Cu and/or Zn, h is from 0.1 to 50, i is from 0 to 50 and y is a number which is determined by the valency and frequency of the elements in the formula other than oxygen, wherein antimony trioxide or $Sb_2O_4$ is first oxidized in an aqueous medium by means of hydrogen peroxide to an Sb(V) compound, an ammoniacal aqueous solution of zinc carbonate or copper carbonate is added to the resulting aqueous suspension and the mixture obtained is dried and is calcined at from 20 to 1200° C.

4. A process for the gas-phase catalytic oxidative preparation of acrylic acid from acrolein, comprising reacting acrylic acid in the presence of a catalytically effective amount of a multimetal oxide as claimed in claim 1 in a gas phase.

5. A process as claimed in claim 4, wherein reaction is conducted at a pressure of 1 to 3 bar, the total space velocity is from 1000 to 3500 l (S.T.P.)/l/h, the temperature is from 230 to 330° C., the acrolein:oxygen:steam:inert gas volume ratio is 1:(1 to 3):(0 to 20):(3 to 30), and the acrolein conversion in a single pass is above 90%.

6. The multimetal oxide material as claimed in claim 1, wherein at least one of $(A)_p$ and $(B)_q$ is in the form of three-dimensional regions having the chemical composition A or B, whose maximum diameters $d_A$ and $d_B$, respectively, are from >0 to 300 µm.

7. The multimetal oxide material as claimed in claim 6, wherein the maximum diameters are from 0.01 to 100 µm.

8. The multimetal oxide material as claimed in claim 6, wherein the maximum diameters are from 0.05 to 50 µm.

9. The multimetal oxide material as claimed in claim 6, wherein the maximum diameters are from 0.05 to 20 µm.

10. The multimetal oxide material as claimed in claim 6, wherein the maximum diameters are from 0.05 to 1.0 µm.

11. The multimetal oxide material as claimed in claim 6, wherein the maximum diameters are from 75 to 125 µm.

12. The multimetal oxide material as claimed in claim 1, wherein regions B comprise crystallites which have the trirutile structure of α- and β-copper antimony $CuSb_2O_6$.

13. The multimetal oxide material as claimed in claim 1, wherein regions B have the pyroclore structure of the mineral partzite.

14. The multimetal oxide material as claimed in claim 1, wherein regions B consist of crystallites which have the structure of copper antimony $Cu_9Sb_4O_{19}$.

* * * * *